US005520666A

United States Patent [19]
Choudhury et al.

[11] Patent Number: 5,520,666
[45] Date of Patent: May 28, 1996

[54] VALVED INTRAVENOUS FLUID LINE CONNECTOR

[75] Inventors: Hrishikesh Choudhury, Gurnee; R. Hayes Helgren, Mundelein; Charles C. Valentincic, Waukegan, all of Ill.

[73] Assignee: Abbott Laboratories, Abbott Park, Ill.

[21] Appl. No.: 350,370

[22] Filed: Dec. 6, 1994

[51] Int. Cl.⁶ .................................................. A61M 25/00
[52] U.S. Cl. .................................... 604/283; 604/905
[58] Field of Search .............................. 137/605; 604/30, 604/33, 167, 169, 170, 249, 283, 905

[56] References Cited

U.S. PATENT DOCUMENTS

| | | | |
|---|---|---|---|
| 3,986,508 | 10/1976 | Barrington | 128/214.2 |
| 4,512,766 | 4/1985 | Vailancourt | 604/169 |
| 4,998,927 | 3/1991 | Vaillancourt . | |
| 5,108,380 | 4/1992 | Helitze et al. | 604/283 |
| 5,269,771 | 12/1993 | Thomas et al. | 604/213 |

*Primary Examiner*—Corrine M. Maglione
*Assistant Examiner*—N. Kent Gring
*Attorney, Agent, or Firm*—A. Nicholas Trausch

[57] ABSTRACT

A valve including a substantially rigid cannula and a valve member positioned for operable communication with the cannula. The valve member is formed from a substantially resilient material, having a slit extending therethrough, and movable with respect to the cannula between a first closed position and a second open position. The slit is substantially closed by the resiliency of the material of the valve member when the valve member is positioned in the first closed position and the cannula cooperates to extend through the slit during movement of the valve member from the first closed position to the second open position to establish a fluid flow path through the cannula and the valve member. A sealing member is also provided independent from a flow of fluid within the fluid flow path to provide positive sealing of the slit when the valve member is positioned in the first closed position.

19 Claims, 2 Drawing Sheets

VALVED INTRAVENOUS FLUID LINE CONNECTOR

TECHNICAL FIELD

The present invention relates generally to valved, fluid line connectors, and more particularly, to a valve for use in a connector or adaptor that attaches two medical implements or components, such as a syringe and a female luer adaptor, to provide a flow of fluid for parenteral administration from the syringe to the female luer where the valve prevents fluid flow before assembly of the connector, enables attachment of the components and subsequent fluid flow therebetween, and automatically provides a positive seal, independent of the fluid flow, upon disassembly of the components.

BACKGROUND OF THE INVENTION

In parenteral administration of fluids, a number of medical implements or components typically are readily interconnected at the point of administration to provide a flow of the desired fluid or medicament from a container, such as a syringe, vial or the like, to a patient. Such components typically include various connectors, adaptors, valves and fluid lines.

For example, a syringe or other container typically is connected to a drug administration set, such as an intravenous fluid line or I.V., to dispense the syringe fluid or medicament into the. I.V. set. The I.V. set in turn is connected to a venipuncture device for administration of the fluid or medicament into the blood stream of the patient.

To connect the syringe to the I.V. set, a connector or adaptor is utilized which typically is first secured to the syringe and then to a port or connector of the I.V. set. Upon assembly of the syringe to the connector, a valve within the connector typically is activated to enable flow of fluid or medicament out of the syringe, through the connector and into the I.V. set.

An example of such an adaptor is disclosed in International Application No. PCT/US92/10367 (International Publication No. WO 93/11828) which provides a medical valve having a reusable seal cap, with or without a precut slit, that may be repeatedly pierced by a sharp pointed tip of a spike contained within the valve. To reseal the aperture formed by the spike or the precut slit within the seal cap after disconnection of the medical valve, the seal cap includes an integrally formed pressure responsive member and associated annular space.

The annular space is filled with fluid under pressure, such as the blood pressure of a patient to which the medical valve is attached. The fluid presses against the pressure responsive member to close the aperture or precut slit.

Such a resealing feature, however, depends on a flow of fluid under pressure which is not available in many applications. Additionally, even when such fluid pressure exits, sealing of the seal cap frequently is inadequate, which can cause leakage and possible contamination.

It therefore would be desirable to provide a valve for use with a medical component, such as an adaptor or connector, that can be utilized to establish a flow of fluid or medicament between two components of a parenteral fluid delivery system and provides an automatic, positive seal, independent of the fluid flow, upon disassembly of the components to prevent leakage and reduce contamination.

SUMMARY OF THE INVENTION

The invention provides a valve for use within a housing of a medical component, such as a connector or adaptor of a parenteral fluid delivery system. The valve includes a substantially rigid cannula mounted within the housing and a valve member positioned within the housing for operable communication with the cannula.

The valve member is formed from a substantially resilient material having a slit extending therethrough and is movable within the housing between a first closed position and a second open position. The slit is substantially closed by the resiliency of the material of the valve member when the valve member is positioned in the first closed position.

The cannula cooperates to extend through the slit during movement of the valve member from the first closed position to the second open position to establish a fluid flow path through the cannula and the valve member. A sealing member is also provided which is independent from a flow of fluid within the fluid flow path and automatically provides positive sealing of the slit when the valve member is positioned in the first closed position.

In a preferred form of the valve, the cannula is a blunt cannula and a spring bias is provided between the valve member and the housing for maintaining the valve member in the first closed position when not in use and automatically returning the valve member to the first closed position from the second open position upon disassembly of the valve member from another component or fluid delivery system. Additionally, the valve member preferably includes a portion thereof for activation by a male luer member for providing movement between the first and second positions, where the portion is accessible from an exterior of the housing for cleaning before and after use to maintain aseptic conditions.

The housing of the valve member typically is formed as a connector or adaptor having connecting portions for attachment between the desired medical components. The valve member and housing preferably cooperate to provide the desired sealing which can be enhanced by appropriate modification of the valve member.

Numerous other advantages and features of the present invention will become readily apparent from the following description of the invention, the claims and the accompanying drawings.

DESCRIPTION OF THE PREFERRED EMBODIMENTS

While this invention is susceptible of embodiment in many different forms, the specification and the accompanying drawings disclose one or more forms as examples of the invention. The invention is not intended to be limited to the embodiments described, the scope of the invention being pointed out in the appended claims.

For ease of description, the device of this invention is described in a typical operating position and terms such as upper, lower, horizontal etc. are utilized with reference to this position. It will be understood, however, that the device of this invention may be manufactured, stored, transported, and sold in an orientation other than the position described.

Some of the figures illustrating the embodiments of the device of the present invention show conventional components, structural details and mechanical elements that will be recognized by one skilled in the art. The detailed descriptions of such elements, however, are not necessary to an understanding of the invention and, accordingly, are not presented herein.

Figure 1:
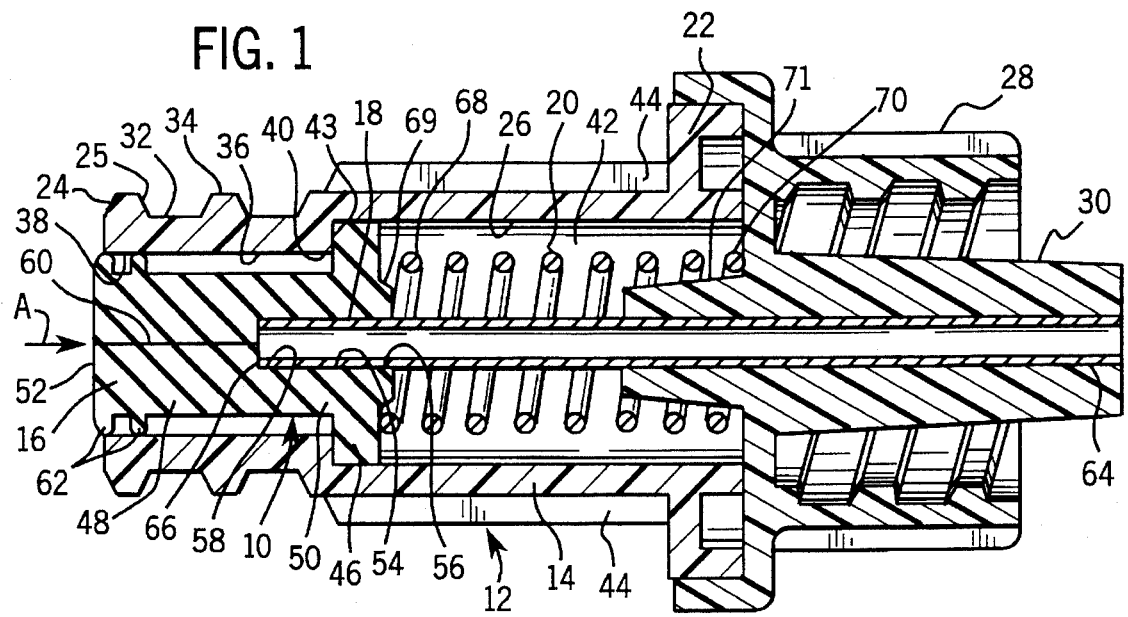
FIG. 1 is a longitudinal cross-sectional view of an embodiment of a valve of the invention illustrated in its closed position within a housing of a medical component.

Referring to FIG. 1, an embodiment of the valve of the invention is generally designated by the reference numeral 10. The valve 10 is illustrated for use within a medical component of a fluid or medicament delivery system, such as a connector or adaptor 12. It is to be understood, however, that the valve 10 can be utilized with a variety of components without departing from the teachings of the present invention.

The valve 10 is preferably secured within a housing 14 of the connector 12 and substantially includes a valve or stopper member 16, a cannula 18 and a spring 20. Although the connector 12 is preferably designed as a one-way fluid connector for flow of fluid or medicament from the left to right with respect to FIG. 1, it is to be understood that the direction of fluid flow as well as the particular details, size and shape of the connector 12 can vary, including providing for two-way fluid flow if desired.

Figure 2:
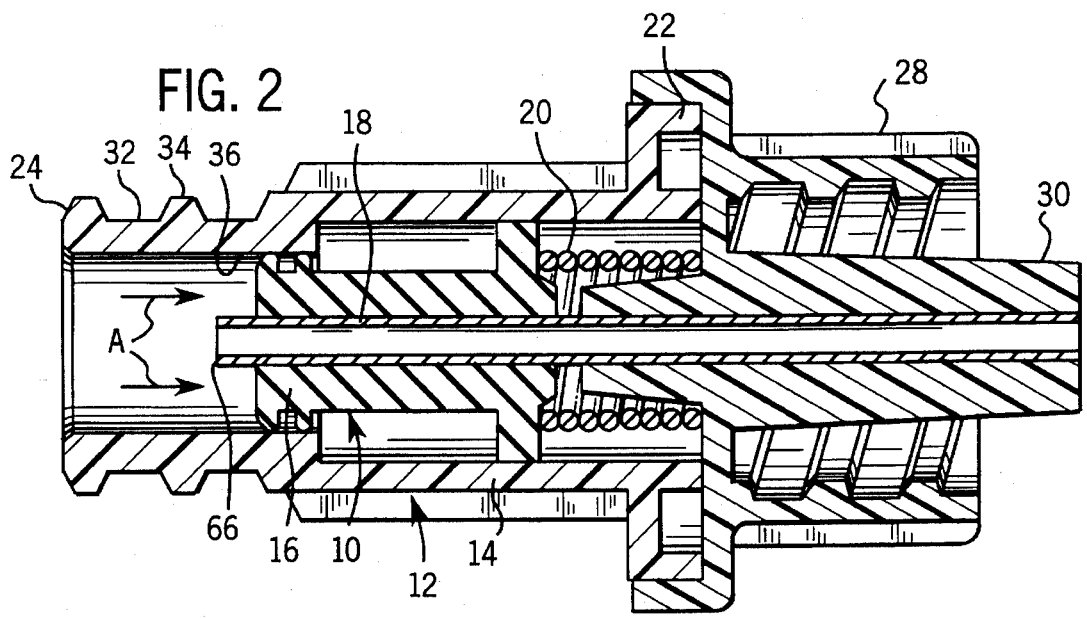
FIG. 2 is a longitudinal cross-sectional view of the valve and housing of FIG. 1 illustrating the valve in its open position.

Briefly, in operation, upon connection of a male tipped luer syringe (not illustrated) to a second end 24 of the housing 14, the valve member 16 is moved in the direction of arrow "A" from a first closed position, illustrated in FIG. 1, to a second open position, illustrated in FIG. 2. During such movement, the cannula 18 extends through a slit formed within the valve member 16 to enable fluid flow from the syringe connected to the second end 24 to a connector member 28 secured to a first opposite end 22 of the housing 14.

Upon disconnection of the male luer from the second end 24, the valve member 16 automatically returns to the first closed position due to the force of the spring 20 and the valve member 16 automatically positively seals the slit to prevent further flow of fluid therethrough. Details of the structure of the valve 10 and the connector 12 will now be provided.

The housing 14 preferably includes first and second opposite ends 22 and 24 and an internal chamber 26 within which the valve 10 is secured. The first end 22 includes the threaded male connector member 28 having a central tapered engagement column 30 for connection to a patient, through I.V. set tubing or the like.

Preferably, the male connector member 28 is formed as a separate member and is secured to the first end 22 of the housing 14 such as by welding (preferably sonic welding), with an adhesive or in any desired way. Alternatively, the male connector member 28 can be integrally formed with the first end 22 of the housing 14. The second end 24 of the housing 14 is formed as a female connector member 25 for accepting the male tipped luer syringe.

It is to be noted that any type of fluid, medicament or blood flow line can be connected to the female connector member 25. For ease of description, the present invention will be described with respect to the male end of a syringe being connected to the female connector member 25 of the second end 24 and a female luer being connected to the male connector member 28 of the first end 22 where the female luer is in communication with a parenteral fluid delivery system, such as an I.V. set. The syringe, female luer and I.V. set are omitted from the drawings for brevity.

An exterior surface 32 of the second end 24 is preferably formed to include one or more ears, threads or similar members 34 for connection of a male luer lock connector or the like. A substantially cylindrical portion 36 of the internal chamber 26 is included with the second end 24 and preferably extends inward from a first outside end 38 to a second inside end 40.

The second inside end 40 of the cylindrical portion 36 communicates with a central, substantially cylindrical portion 42 of the chamber 26 which extends the remaining length of the housing 14 to the first end 22. A shoulder 43 is formed between the cylindrical portion 36 and the central portion 42 for engagement with the valve member 16 against the force of the spring 20 as described below. To readily grip the connector 12 during use, one or more engagement ribs 44 can be formed on an exterior surface of the housing 14.

The valve member 16 has a T-shaped cross-sectional configuration and is substantially circular in shape so that it can be rotated within the housing 14 without degrading the sealing capabilities of the valve member 16. The valve member 16 thus includes a first end 46 forming a top of the "T" and a base portion 48 having a first end 50 integrally formed to one side of the first end 46 and a second end 52.

In order to provide the desired sealing, the valve member 16 is preferably formed from a substantially resilient material such as rubber, silicone or the like. The particular material of the valve member 16, however, can vary so long as the valve member 16 functions as described herein.

In order to secure the cannula 18 to the valve member 16 when positioned in the first closed position of FIG. 1, the first end 46 and the base 48 of the valve member 16 includes a channel 54 formed therein. The channel 54 is formed with a diameter slightly less than the diameter of the cannula 18 for engagement therewith and extends within the valve member 16 from a first outside end 56 to a second inside end 58.

In order for the cannula 18 to extend through the valve member 16, a slit 60 is formed through the valve member 16 which extends from the end 52 to the second inside end 58 of the channel 54. The slit 60 preferably has a length corresponding to approximately one-half the circumference of the cannula 18, but can vary.

Alternatively, the channel 54 can be omitted and the valve member 16 can be lengthened, if desired, with the slit 60 extending therethrough. In such an arrangement, the cannula 18 pierces through the slit 60 and partially penetrates the valve member 16 in the closed position of FIG. 1.

To provide positive sealing of the slit 60, the end 52 of the base 48 of the valve member 16 preferably includes one or more circumferential, outwardly extending lips 62 formed thereabout. The lips 62 engage the surface of the cylindrical portion 36 of the housing 14 to ensure closing of the slit 60, particularly when the valve 10 is in the first closed position illustrated in FIG. 1. Additionally, the lips 62 provide a "wiper seal" to prevent contaminants from lodging between the stopper member 16 and the housing 14.

In order to vary the sealing abilities of the valve member 16, the size and shape of the lips 62 can vary. For example, the lips 62 can be increased in size or have different shapes, while the cylindrical portion 36 typically does not vary since its dimensions are set by appropriate standards.

The lips 62 also assist in providing a strong grip on the cannula 18 during movement of the valve 10 to the second open position of FIG. 2 and maintain that grip for as long as the valve 10 is positioned therein. As the valve 10 moves to the second open position, the lips 62 slide along the cylindrical portion 36 of the housing 14 and slightly flex and/or compress against the cylindrical portion 36 to accommodate the cannula 18 within the slit 60.

To prevent the valve member 16 from being expelled from the housing 14 against the force of the spring 20 in the closed position of FIG. 1, the end 46 of the valve member 16 engages the shoulder 43 of the housing 14.

The cannula 18 includes a first end 64 connected to the male connector 28 and a second opposite end 66 for extension through the slit 60. The cannula 18 is preferably blunt and made of rigid material to accept frictional loads due to sealing without buckling.

If a plastic penetrator or cannula (not illustrated) is utilized, it must be conical or pointed for strength and stability during insertion through a slit. Such a conical plastic penetrator, however, does not enable good resealing since when a stopper is compressed about the conical penetrator, the slit is enlarged and the stopper material can experience a higher compression set.

For example, when a conical penetrator is inserted through a slit of a stopper, the farther the conical penetrator is inserted, the larger the slit is expanded due to the increasing diameter of the conical penetrator. When opened farther than necessary or held open for an extended period of time, the material of the stopper obtains a compression set which inhibits its sealing abilities when the stopper is returned to the closed position.

To provide a spring bias to the valve 10 and urge the valve member 16 to the first closed position when disconnected from the male luer, the spring 20 is positioned within the central portion 42 of the chamber 26 of the housing 14. The spring 20 surrounds the cannula 18 and is seated at a first end 68 about a seat portion 69 formed on the first end 46 of the valve member 16 and at a second end 70 about a conical portion 71 integrally formed with the male connector member 28.

Accordingly, when the valve member 16 is moved from the first closed position to the second open position by insertion of the male luer, the spring 20 is compressed as illustrated in FIG. 2. Upon removal of the male luer, the spring 20 automatically returns the valve member 16 to the first closed position illustrated in FIG. 1.

In operation, the male luer tip of a full syringe without a needle (not illustrated) is preferably connected to the female connector member 25. The female luer on an I.V. line is then connected to the male connector member 28.

If desired, however, the female luer can be connected first. In either event, the end 52 of the valve member 16 is preferably cleaned or swabbed before connecting the male luer thereto, to maintain aseptic conditions.

As the male luer is inserted against the end 52 of the valve member 16, the valve member 16 moves in the direction of arrow "A". During such movement, the second end 66 of the cannula 18 is forced through the slit 60 and causes flexing and compression of the lips 62 against the cylindrical portion 36 of the housing 14.

Upon full insertion of the male luer and locking engagement of the male luer to the housing 14, the spring 20 is compressed and the second end 66 of the cannula 18 extends out of the end 52 of the valve member 16 for communication with the flow path of the male luer. The syringe can then be activated to discharge the medicament into and through the valve member 16 by the passage or channel 54 of the cannula 18 to the male connector portion 28 and the I.V. line to the patient.

Once the syringe is empty, the male luer can be disconnected which automatically returns the valve member 16 to the closed position by the force of the spring 20. At the same time, the slit 60 is positively sealed by the lips 62 which engage the cylindrical portion 36 of the housing 14 and circumferentially support the end 52 of the valve member 16 to thereby provide a positive mechanical seal to the material of the valve member 16.

Figure 3:
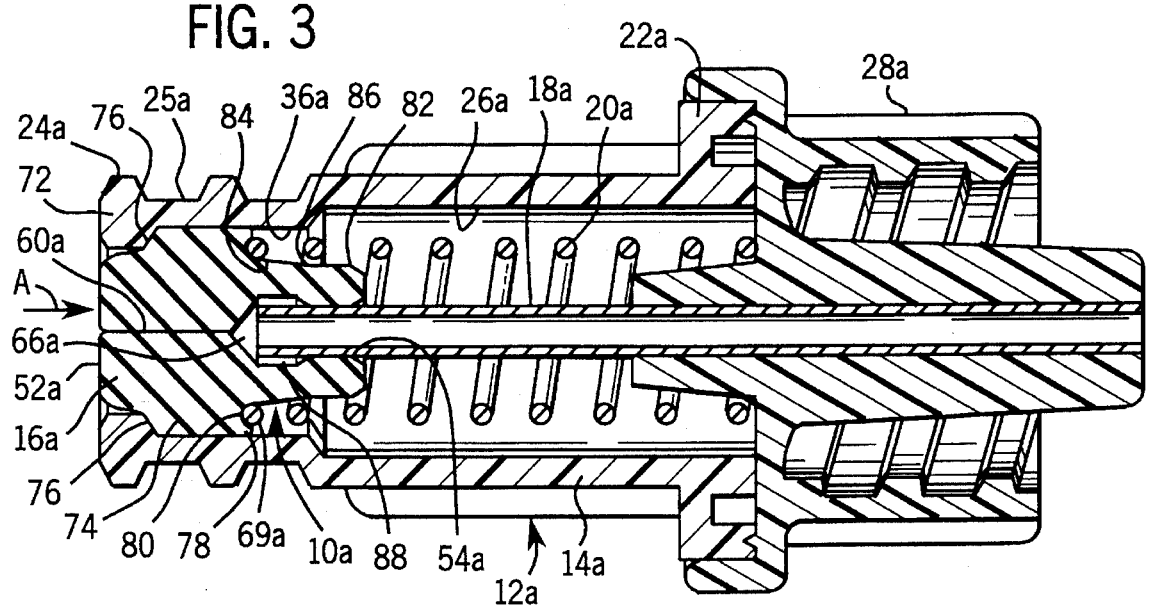
FIG. 3 is a longitudinal cross-sectional view of another embodiment of the valve of the invention illustrated in its closed position within a housing of a medical component.
Figure 4:
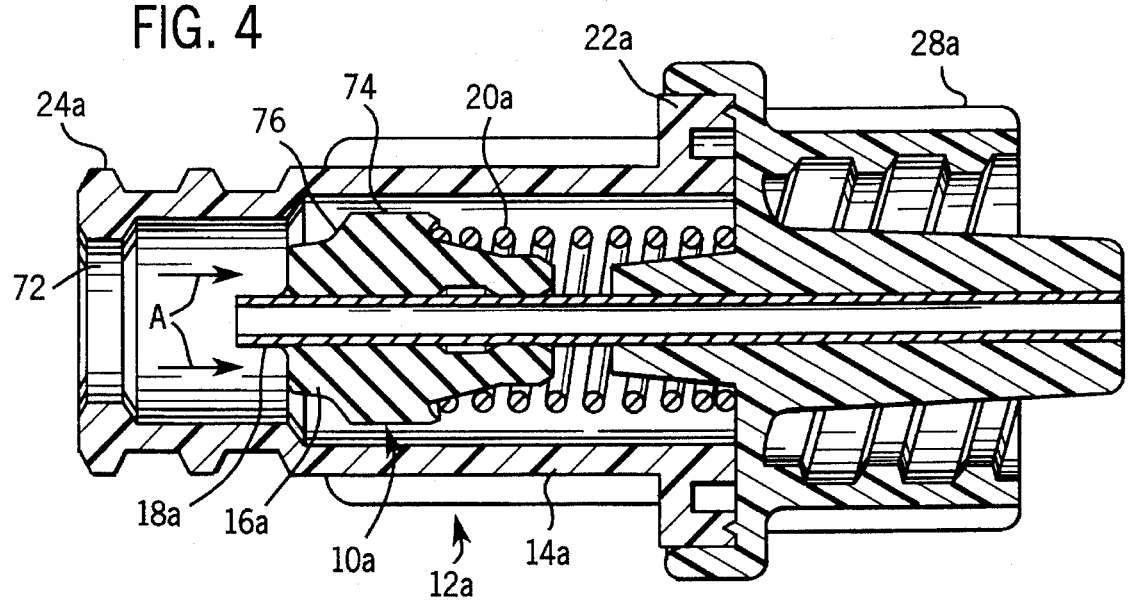
FIG. 4 is a longitudinal cross-sectional view of the valve and housing of FIG. 3 illustrating the valve in its open position.

FIGS. 3 and 4 illustrate another embodiment of the valve of the present invention designated generally by the reference numeral 10a where similar elements are identified with the same reference numerals including a subscript "a". In this embodiment, the cylindrical portion 36a of the housing 14a is formed with an internal collar 72 and the valve member 16a does not have a T-shaped cross-sectional configuration or a lip 62 but includes an outwardly extending annular portion 74 about its midsection.

The annular portion 74 also includes a first tapered end 76 for engagement with the collar 72 to prevent the valve member 16a from being forced out of the housing 14a against the force of the spring 20a. The engagement of the tapered end 76 with the collar 72 also mechanically assists radial sealing of the slit 60a in the closed position of FIG. 3 since the tapered end 76 is forced inward toward the slit 60a from contact with the collar 72 against the force of the spring 20a.

A second opposite end 78 of the annular portion 74 includes an annular recess 80 for seating of the first end 69a of the spring 20a. An end portion 82 of the valve member 16a opposite the end 52a has a reduced diameter which is accepted within the confines of the spring 20a. The end portion 82 is also slightly tapered from a first end 84 proximate the annular portion 74 to a second end 86 which extends within the spring 20a toward the male connector 28a. The internal diameter of spring 20a is smaller than the diameter of annular portion 82 at first end 84 so that an interference fit is achieved giving a radial sealing force of the slit 60a onto the cannula 18a at the end opposite 52a.

The channel 54a of the valve member 16a includes an enlarged diameter recess 88 forming the second inside end 66a of the channel 54a. The recess 88 provides a degree of flexibility to the end portion 82 for increased sealing engagement against the cannula 18a provided by the engagement of the spring 20a with the tapered end portion 82. To further enhance sealing of the end portion 82 against the cannula 18a, the diameter of the end portion 82 within the confines of the spring 20a can be enlarged.

The operation of this embodiment is similar to the embodiment of FIGS. 1 and 2. In this embodiment, however, sealing of the slit 60a is enhanced by the radial sealing provided by the engagement between the tapered end 76 of the valve member 16 with the collar 72 of the housing 14a against the force of the spring 20a. Sealing is also enhanced by the spring I.D. constriction. Additionally, the diameter of the annular portion 74 can be modified to minimize frictional contact with the wall of the cylindrical portion 36a of the housing 14a, such as by tapering or otherwise modifying the annular portion 74.

It will be readily apparent from the foregoing detailed description of the invention and from the illustrations

What is claimed is:

1. A valve, comprising:

a substantially rigid cannula;

a valve member connected for operable communication with said cannula, said valve member being formed from a substantially resilient material having a slit extending therethrough and movable with respect to said cannula between a first closed position and a second open position, said slit being substantially closed by the resiliency of said material of said valve member when said valve member is positioned in said first closed position, said cannula cooperating to extend through said slit during movement of said valve member from said first closed position to said second open position to establish a fluid flow path through said cannula and said valve member; and sealing means located on the valve member independent from a flow of fluid within said fluid flow path for automatically providing radially inward circumferential support for positive sealing of said slit when said valve member is positioned in said first closed position.

2. The valve in accordance with claim 1 wherein said cannula is a blunt cannula.

3. The valve in accordance with claim 1 including spring means for maintaining said valve member in said first closed position when said valve member is not in use and for automatically returning said valve member to said first closed position from said second open position upon disconnecting said valve member from a fluid line component.

4. The valve in accordance with claim 3 wherein said spring means are integrally formed as a portion of said valve member.

5. The valve in accordance with claim 3 wherein said spring means are a helical spring member.

6. The valve in accordance with claim 1 wherein said valve member is activated by a male luer member connected thereto to provide movement between said first and second positions.

7. The valve in accordance with claim 1 wherein at least a portion of said valve member is accessible for cleaning thereof.

8. A connector for an intravenous fluid line, comprising:

a housing;

a substantially rigid cannula mounted within said housing;

a valve member positioned within said housing for operable communication with said cannula, said valve member being formed from a substantially resilient material having a slit extending therethrough and being movable within said housing between a first closed position and a second open position, said slit being substantially closed by the resiliency of said material of said valve member when said valve member is positioned in said first closed position, said cannula cooperating to extend through said slit during movement of said valve member from said first closed position to said second open position to establish a fluid flow path through said cannula and said valve member; and sealing means located on the valve member independent from a flow of fluid within said fluid flow path for automatically providing radially inward circumferential support for positive sealing of said slit when said valve member is positioned in said first closed position.

9. The connector in accordance with claim 8 wherein said cannula is a blunt cannula.

10. The connector in accordance with claim 8 including spring means for maintaining said valve member in said first closed position when said valve member is not in use and for automatically returning said valve member to said first closed position from said second open position upon disconnecting said valve member from the intravenous fluid line.

11. The connector in accordance with claim 10 wherein said spring means are integrally formed as a portion of said valve member.

12. The connector in accordance with claim 10 wherein said spring means are a helical spring member.

13. The connector in accordance with claim 10 wherein said valve member includes a portion for cooperative engagement with an inside diameter of said spring to seal said valve member against said cannula.

14. The connector in accordance with claim 8 wherein said valve member is activated by a male luer member connected thereto to provide movement between said first and second positions.

15. The connector in accordance with claim 8 wherein at least a portion of said valve member is accessible from the exterior of the housing for cleaning thereof.

16. The connector in accordance with claim 8 wherein said sealing means include a portion of said valve member having a predetermined configuration selected for cooperative sealing engagement with a portion of said housing to provide said automatic positive sealing of said slit.

17. The connector in accordance with claim 16 wherein said portion of said valve member is an outwardly extending lip integrally formed with said resilient material of said valve member.

18. The connector in accordance with claim 16 wherein said portion of said valve member is a tapered engagement portion integrally formed with said resilient material of said valve member.

19. The connector in accordance with claim 8 including first and second connection means for attaching desired medical components thereto and establishing a flow path therebetween.

* * * * *